United States Patent [19]

Gingrich et al.

[11] Patent Number: 6,046,453

[45] Date of Patent: Apr. 4, 2000

[54] AGENT IDENTIFICATION FOR ANESTHETIC GAS MONITORS USING MINIMUM ALVEOLAR CONCENTRATION (MAC) VALUES

[75] Inventors: Matthew A. Gingrich, Westminster; Donald W. Heckel, Brighton; Paul B. Batchelder, Golden, all of Colo.

[73] Assignee: Datex-Ohmeda, Inc., Tewksbury, Mass.

[21] Appl. No.: 09/042,312

[22] Filed: Mar. 13, 1998

[51] Int. Cl.[7] .......................... G01N 21/35; G01N 21/17
[52] U.S. Cl. ...................................... 250/343; 250/339.13
[58] Field of Search ..................... 250/339.13, 339.01, 250/339.02, 339.06, 339.07, 339.12, 343; 600/532

[56] References Cited

U.S. PATENT DOCUMENTS

| | | |
|---|---|---|
| 4,150,670 | 4/1979 | Jewett et al. ............................. 128/188 |
| 4,784,486 | 11/1988 | Van Wagenen et al. ................ 356/301 |
| 4,914,719 | 4/1990 | Conlon et al. ........................... 250/339 |
| 5,050,615 | 9/1991 | Malkamaki . |
| 5,111,827 | 5/1992 | Rantala . |
| 5,296,706 | 3/1994 | Braig et al. .............................. 250/339 |
| 5,479,019 | 12/1995 | Gross . |
| 5,714,759 | 2/1998 | Nelson . |
| 5,731,581 | 3/1998 | Fischer et al. . |
| 5,800,361 | 9/1998 | Rayburn . |

*Primary Examiner*—Constantine Hannaher
*Assistant Examiner*—Albert Gagliardi
*Attorney, Agent, or Firm*—Holme Roberts & Owen LLP

[57] ABSTRACT

An apparatus and method for identifying one anesthetic agent contained in an anesthetic gas sample as the primary anesthetic agent and for identifying a second anesthetic agent as the secondary anesthetic agent is based on the use of minimum alveolar concentration (MAC). The primary agent is identified as the anesthetic agent which has the highest percent of its MAC at its measured volume concentration. The secondary agent is identified as the anesthetic agent which has the second highest percentage of its MAC at its measured volume concentration. Certain minimum threshold levels must be met before an anesthetic agent is identified either as the primary or secondary agent.

11 Claims, 4 Drawing Sheets

AGENT IDENTIFICATION FOR ANESTHETIC GAS MONITORS USING MINIMUM ALVEOLAR CONCENTRATION (MAC) VALUES

BACKGROUND OF THE INVENTION

This invention relates to anesthetic gas agent monitors that are used to accurately identify anesthetic agents in a anesthetic gas sample obtained from an anesthetized patient as well as to provide an indication of their relative concentrations.

In the field of medical monitoring equipment it is desired to produce an apparatus for measuring the concentration of anesthetic agents in a respiratory gas sample that is inexpensive, simple to use, accurate and fast in its measurements of anesthetic gas concentrations and the identification of the primary and secondary anesthetic agents. In the field of anesthesiology, there are a number of commonly used anesthetic agents including nitrous oxide, halothane, enflurane, isoflurane, sevoflurane and desflurane. The concentrations of these anesthetic agents are most often measured by an infrared anesthetic agent monitoring apparatus which operates by measuring the optical transmissivity of a respiratory gas sample at certain wavelengths of light. One such anesthetic agent measurement apparatus is disclosed in commonly assigned U.S. Pat. Nos. 5,731,581 and 5,714,759 which disclosures are hereby incorporated by reference. The resultant measurements are processed to identify one of the known anesthetic agents that is contained in the gas sample as well as its concentration.

Infrared anesthetic agent monitoring apparatus generally perform two functions: the identification of the anesthetic agent or agents present in the respiratory gas sample and the determination of the concentration of the identified anesthetic agent or agents. These two functions may be performed either by two separate sets of circuitry in the apparatus or by a common set of circuitry. These apparatus are determined systems, with the number of spectral filters used therein being greater than or equal to the number of anesthetic agents that the apparatus is designed to identify. The selection of the wavelengths passed by the spectral filters is driven by the desire to use wavelengths that are strongly and uniquely absorbed by the anesthetic agents in question. Beer's Law (A=ECL) teaches that the light absorbance exhibited by a respiratory gas sample is substantially linearly related to the concentration of the anesthetic agent contained in the respiratory gas sample. Since the terms E and L in this equation are constants, the presence and partial pressure of the anesthetic agent are determined by monitoring wavelength specific light absorbance values. If each anesthetic agent absorbed energy at only one of the selected wavelengths, the analytical task is simple in that the concentration of each anesthetic agent linearly follows the light absorbance measured at that one wavelength. However, anesthetic agents are chemically similar and their absorbance spectra generally overlap, exhibiting varying degrees of colinearity. This lack of absorbance uniqueness necessitates measuring light absorbance of the respiratory gas sample at all of the selected wavelengths to identify and quantify the anesthetic agent contained in the respiratory gas sample.

After an anesthetic agent is identified its identity is displayed to the user along with concentration data. If the user, i.e., the anesthesiologist, changes the anesthetic agent being given to a patient then the two agents must both be identified with one as the primary agent and the other as the secondary agent. The primary agent should be the anesthetic which is producing the greatest therapeutic effect or drug response in the patient. A problem arises when volume concentration alone is used to determine the primary and secondary agents. A high volume concentration of a less effective anesthetic agent which was originally given by the anesthesiologist can interfere with the proper identification of a more therapeutically effective second agent as the primary agent until the point when the volume concentration of the earlier given first agent decreases below the volume concentration of the second agent.

SUMMARY OF THE INVENTION

In an anesthetic gas measurement apparatus various anesthetic gas agents and the concentration of the agents is identified. The identification of primary and secondary agents depends on the number of agents and also the minimum alveolar concentrations (MAC's) for the various agents. Minimum alveolar concentrations are the volume concentrations at which fifty percent of the patients are anesthetized. The MAC values used in this invention are those for administration of the agent to the patient in conjunction with oxygen. The use of MAC information for the identification of primary and secondary agents eliminates instances where a less therapeutic anesthetic agent is first used and the identification of a second more effective anesthetic agent as the primary agent is delayed until the volume concentration of the first agent decreases to a lower level than the second agent. If the MAC of the administered anesthetic agents is taken into consideration instead of only the actual volume concentrations then the second gas will be identified as the primary agent more quickly and accurately.

DETAILED DESCRIPTION

Figure 1:
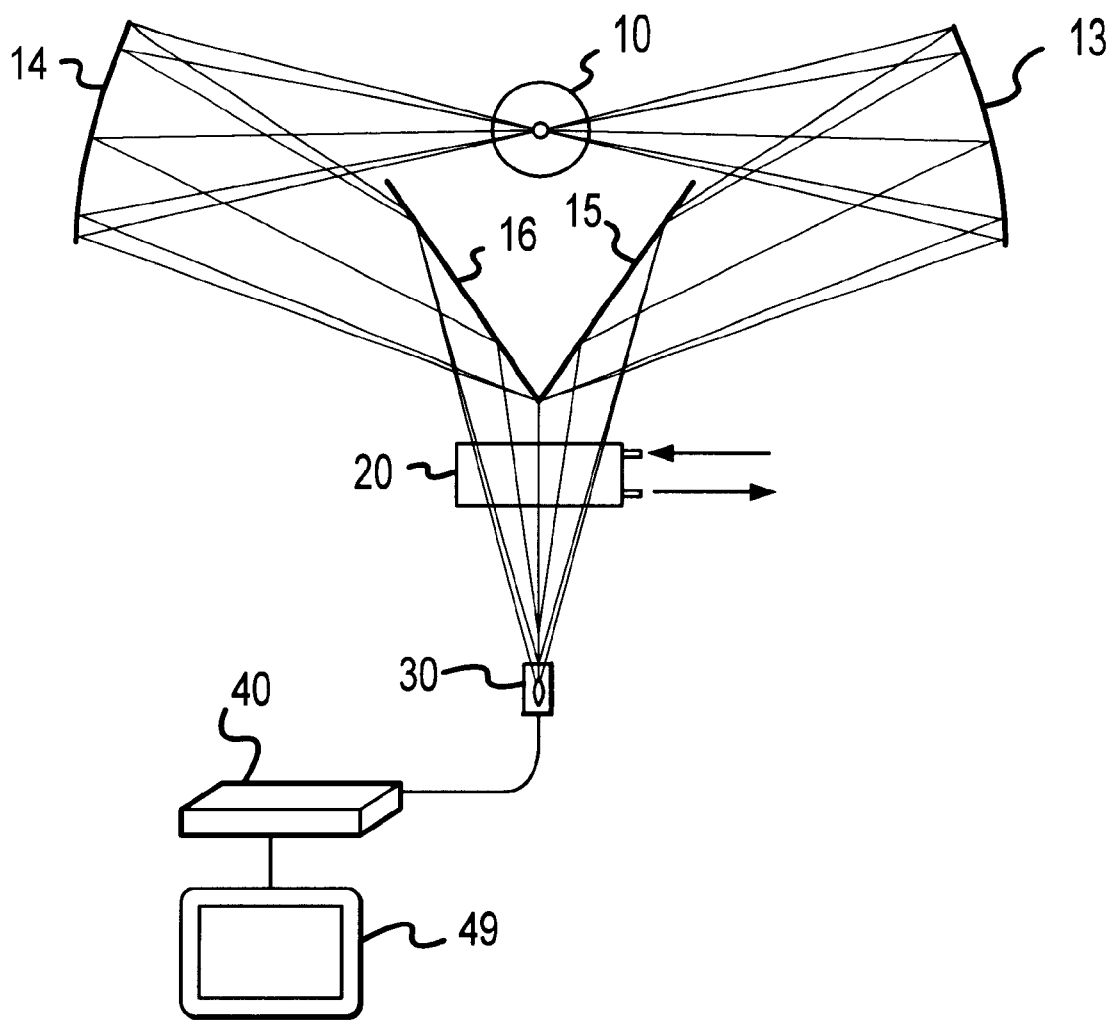
FIG. 1 illustrates, in block diagram form, the overall architecture of the automatic gas sample identification apparatus of the present invention.

FIG. 1 illustrates in block diagram form the overall system architecture of the apparatus for the automatic identification of gas samples. This gas sample identification apparatus 1 functions to both detect the presence and measure the concentration of analytes contained in a gas sample that is passed through a gas chamber 20. The anesthetic agent identification means described herein as the preferred embodiment of the invention represents one application of this inventive concept, and the underlying principles behind this identification method is equally applicable to other applications where one or more analytes are contained in a gas sample, and the presence and concentration of these analytes must be determined with accuracy.

In FIG. 1, the gas sample identification apparatus 1 is illustrated as including a light source 10, mirrors 13–16, gas chamber 20, detector circuit 30 and computation circuit 40. In operation, a gas sample is passed through gas chamber 20 while at least one beam of light produced by light source 10 is transmitted through the gas chamber 20 after reflection from mirrors 13–16. The gas sample has optical transmissivity characteristics that are determined by the type of components contained in the gas sample as well as their concentrations. Therefore, the light beam that passes through the gas sample in gas chamber 20 is optically processed by various filter and detector elements contained in detector 30 to produce electrical signals that can be used by computation circuit 40 to precisely identify the components contained in the gas sample as well as their relative concentrations. In the application of this apparatus to anesthetic agent monitoring, respiratory gases obtained from an anesthetized patient are passed through gas chamber 20 to identify the presence and concentration of carbon dioxide ($CO_2$) as well as the presence and concentration of one or more anesthetic agents in the patient's respiratory gases.

In the field of anesthesiology, there are several commonly used anesthetic agents: nitrous oxide, halothane, enflurane, isoflurane, desflurane and sevoflurane. Therefore, the detector circuit 30 and computation circuit 40 must have the capability to measure subtle differences in optical transmissivity in the gas sample to distinguish between the various anesthetic agents and combinations of anesthetic agents used in various concentrations.

Thus, the data received by detector circuit 30 is processed by computation circuit 40 is to obtain a concentration value for one or more anesthetic gas agents present in the gas sample. The results of this computation are displayed to the user via a display device 49 which presents an identification of the determined component and its concentration in human readable form, such as an alphanumeric readout.

Figure 2:
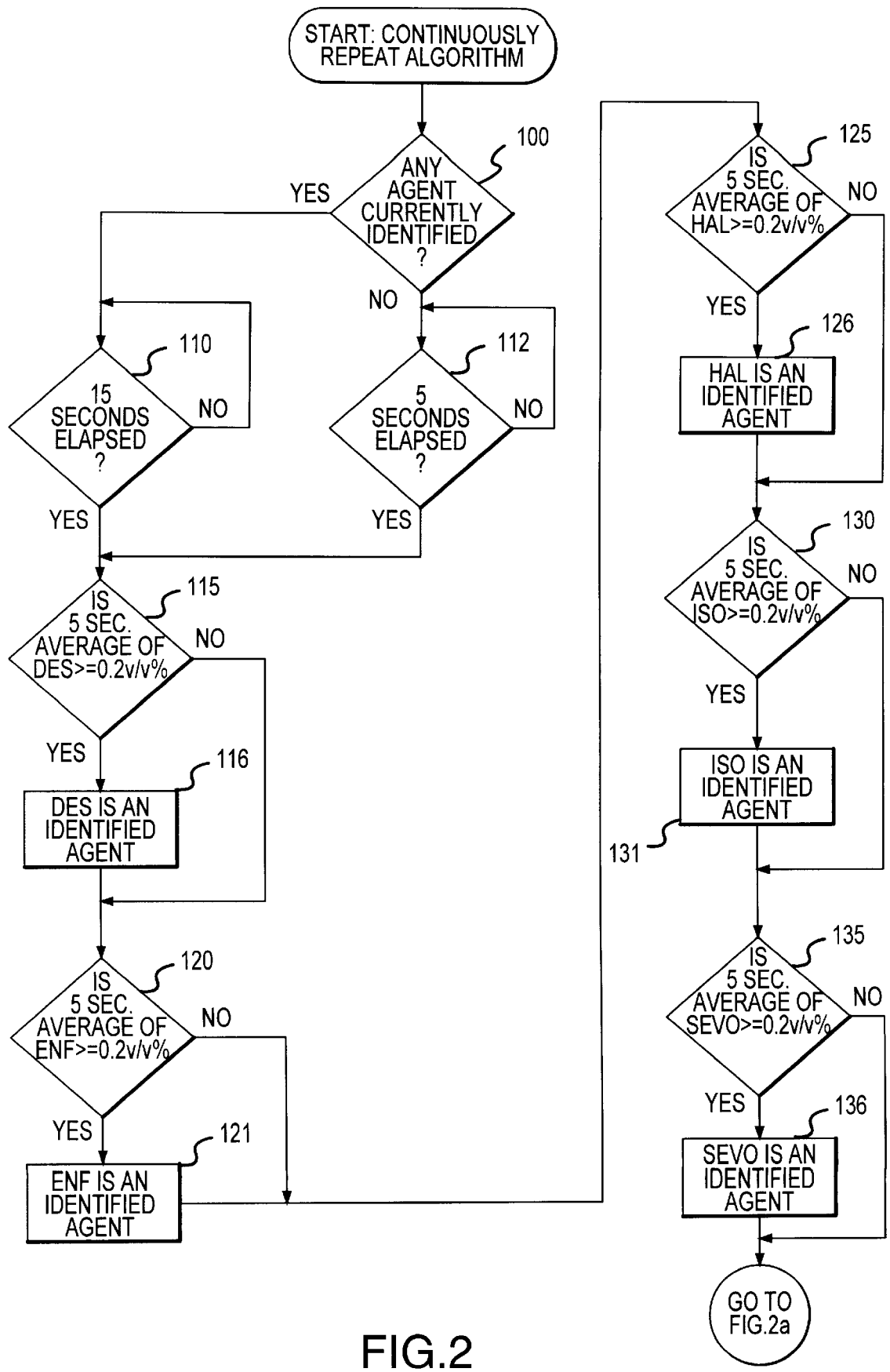
FIGS. 2 and 2a are a block diagram of the algorithm implemented in the anesthetic gas monitor as part of the invention.
Figure 2A:
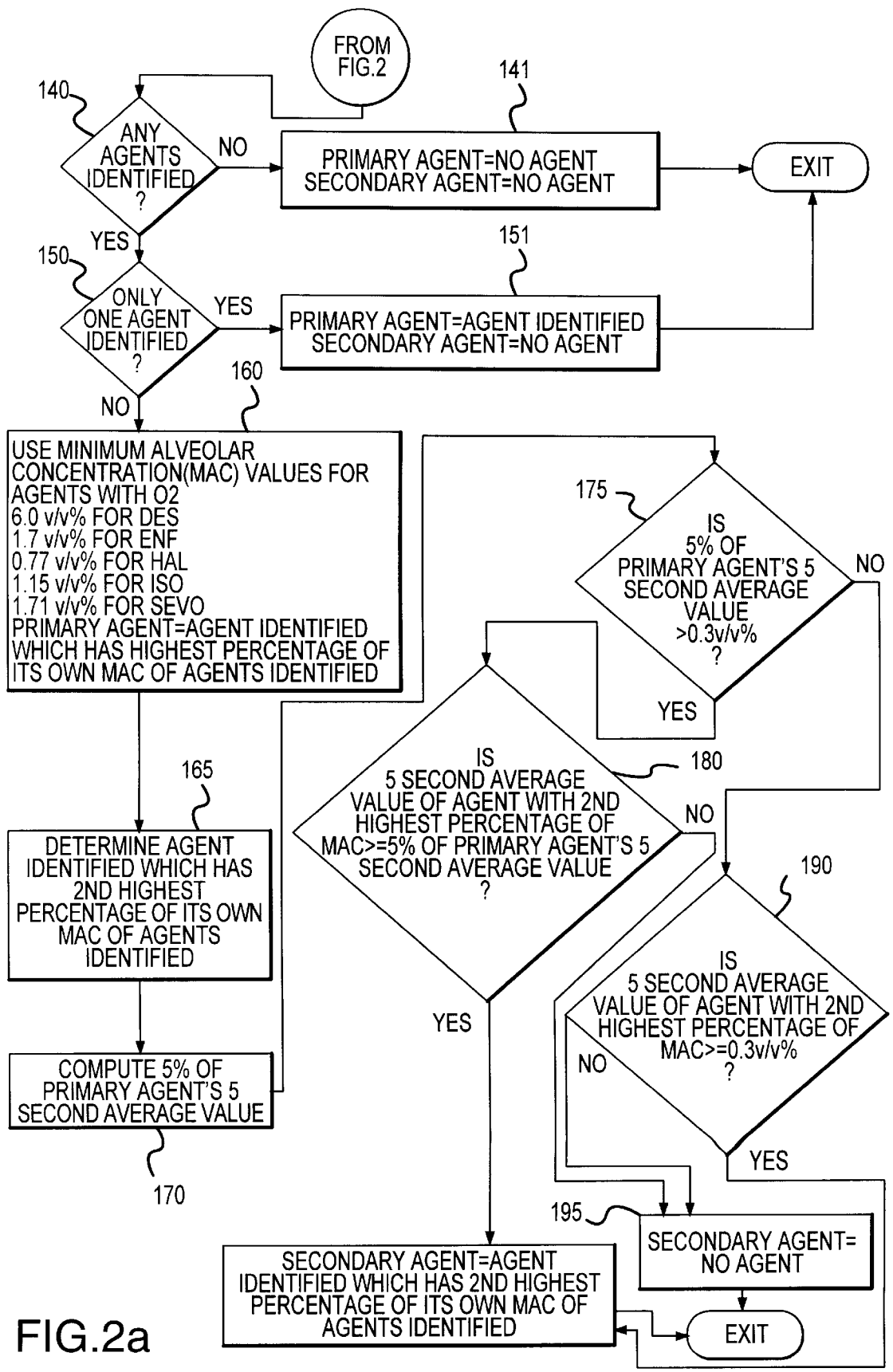

FIGS. 2 and 2a are a block diagram which implements an embodiment of the present invention as a software algorithm executed by the computation circuit 40 prior to display of the anesthetic gas concentrations to the user.

The first step in the post-concentration algorithm is to determine if there has been any anesthetic agent identified by the monitor. If an anesthetic agent has been identified then the elapsed time from initial monitoring must be 15 seconds before continuing with the algorithm as determined in step 110. If an anesthetic agent has not already been identified then the algorithm will continue if the elapsed time from initial monitoring is 5 seconds as determined in step 112. In steps 115, 120, 125, 130 and 135 the minimum volume concentration threshold of 0.2 v/v % is tested for a 5 second running average for each of desflurane (DES), enflurane (ENF), halothane (HAL), isoflurane (ISO) and sevoflurane (SEVO) respectively and if the minimum volume concentration threshold based on the five second running average is met then the respective flag for each is set in steps 116, 121, 126, 131 and 136. A minimum threshold for additional anesthetic agents could be introduced into the algorithm at this point if additional agents become available or widely used.

After identifying the minimum threshold for the agents the algorithm determines the primary and secondary agents through the use of MAC values. If no agents have been identified as determined by step 140 then the primary agent and the secondary agent are both output to the user on display 49 as "NO AGENT." If any anesthetic agent has been identified then the algorithm determines if only one agent has been identified at step 150. The only identified agent is then output to the user on display 49 as the primary agent along with the volume concentration data associated with the identified primary agent and the secondary agent is identified as "NO AGENT" in step 151.

If more than one anesthetic agent has been identified as determined by step 150 then in step 160 the minimum alveolar concentration (MAC) values for the agents in oxygen are used in conjunction with the volume concentrations to determine the primary agent which is then output to the user at display 49. For example, if the volume concentration for desflurane is 4 v/v % and the volume concentration for isoflurane is 1.15 v/v % then isoflurane would be identified as the primary agent because it is 100% of its MAC value whereas desflurane is only at 66% of its MAC value. In step 165 the secondary agent is determined in a like manner, i.e., the agent identified having the second higher percentage of its own MAC.

The MAC values used in the present invention are 6.0 v/v % for desflurane, 1.7 v/v % for enflurane, 0.77 v/v % for halothane, 1.15 v/v % for isoflurane and 1.71 v/v % for sevoflurane. The MAC based data is for use of the agent in oxygen.

After identification of the secondary agent a second threshold determination is made for that agent. The five second running average of the volume concentration for the secondary agent must be either greater than or equal to 0.3 v/v % or greater than or equal to five percent (5%) of the primary agents five second average volume concentration whichever is greater. In order to accomplish this test five percent of the primary agents five second average volume concentration value is computed at step 170. In step 175 the threshold to be used is determined by comparing five percent (5%) of the five second running average of the primary agent to 0.3 v/v %. If the five percent (5%) threshold is greater then it is used in step 180 to determine if the threshold has been met by comparing the five second average of the agent with the second highest percentage of MAC with the computed five percent (5%) of the primary agents five second running average. Otherwise in step 190 the five second running average volume concentration for the agent with the second highest percentage of MAC is compared to the 0.3 v/v % threshold. If the appropriate threshold is met then the secondary agent is identified as that agent having the second highest percentage of its own MAC, otherwise the secondary agent is identified as "NO AGENT."

Figure 3:
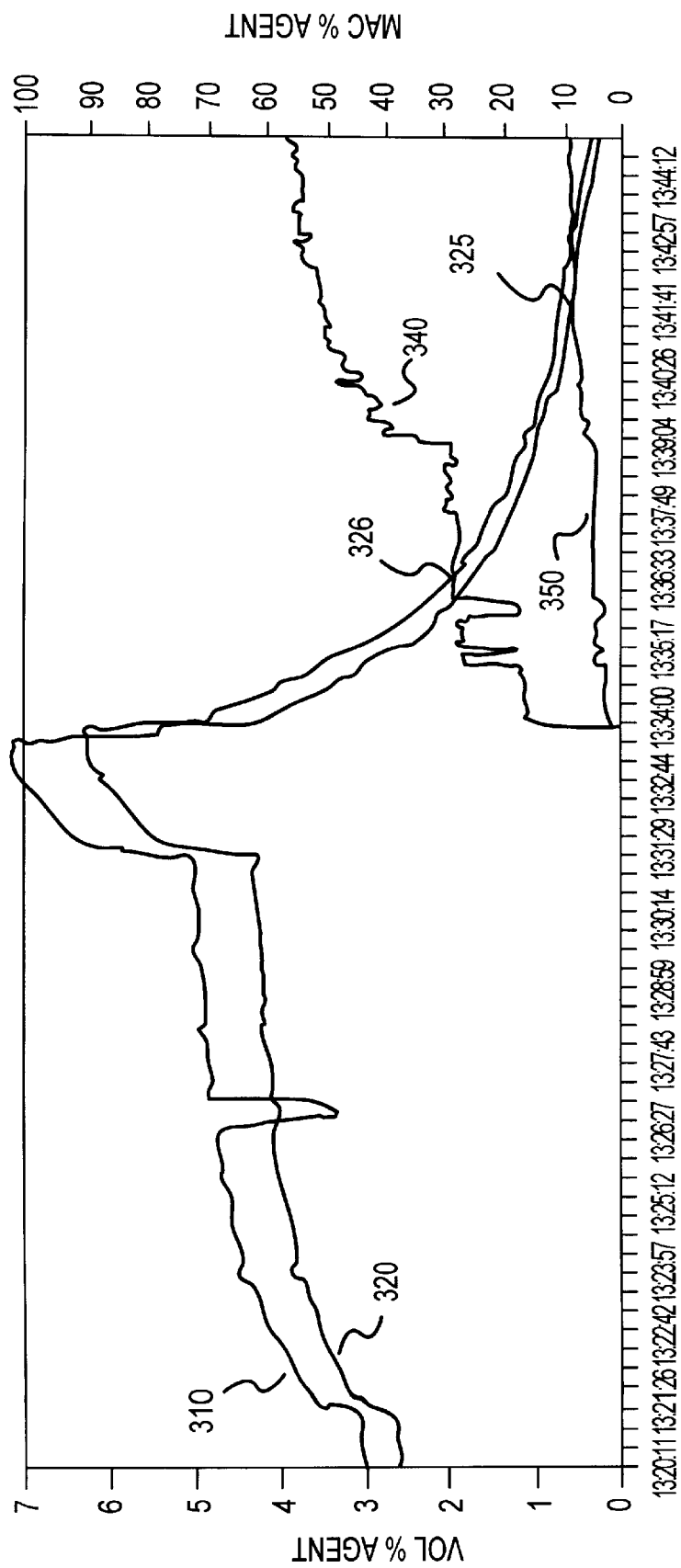
FIG. 3 is a chart depicting the effect of the present invention on anesthetic agent identification.

FIG. 3 is a graph depicting the data used for agent identification and illustrates the improvement through the use of MAC values. DES AVG curve 320 is five second running average for the volume concentration of desflurane which has a MAC of 6.0. DES MAC curve 310 depicts the percent of the MAC value of 6.0 which is represented by the respective volume concentration in DES AVG curve 320. ISO AVG curve 350 is five second running average of the volume concentration of the anesthetic agent isoflurane which has a MAC value of 1.15 v/v %. ISO MAC curve 340 depicts the percent of the MAC value for isoflurane which is represented by the respective volume concentration in ISO AVG curve 350. In prior art systems the primary agent would have been identified as desflurane until the DES AVG curve crossed the ISO AVG curve at point 325, i.e., when the five second running average of the isoflurane volume concentration finally exceeded the five second running average of the desflurane concentration. As can be seen FIG. 3, this is almost 8 minutes after desflurane was no longer administered to the patient and isoflurane began administration at time 13:34:00.

Using the MAC value in the determination of the primary and secondary agent according to the present invention it can be seen in FIG. 3 that the curves 310 and 340 representing the percentages of the respective MAC's for desflurane and isoflurane cross at point 326. Thus, using MAC values the primary agent would be switched from desflurane to isoflurane at time 13:36:33, only two and one-half minutes after the switch from desflurane to isoflurane. This is a significant improvement on the earlier method and apparatus.

While a specific embodiment of this invention has been disclosed, it is expected that those skilled in the art can and will design alternate embodiments of this invention that fall within the scope of the appended claims.

We claim:

1. Apparatus for identifying a plurality of predefined anesthetic agents contained in an anesthetic gas sample comprising:

a chamber adapted to hold the anesthetic gas sample;

a light source for irradiating said anesthetic gas sample with light;

a detector for detecting an intensity of light emanating from said chamber as a result of irradiating said anesthetic gas sample with said light; and a processor for processing said detected intensity to identify a volume concentration of a plurality of said predefined anesthetic agents and for identifying a primary agent and a secondary agent using minimum alveolar concentration values.

2. The apparatus of claim 1 wherein said apparatus further comprises a display for displaying to a user the volume concentrations and identities of said primary agent and said secondary agent.

3. The apparatus of claim 1 wherein said processor further comprises a means for identifying a minimum threshold for said primary agent and said secondary agent.

4. The apparatus of claim 3 wherein said minimum threshold is 0.2 v/v % for said primary agent.

5. The apparatus of claim 3 wherein said minimum threshold for said secondary agent is the greater of 0.3 v/v % or five percent of the volume concentration of said primary agent.

6. Apparatus for identifying a primary agent and a secondary agent from a plurality of anesthetic agents contained in an anesthetic gas sample comprising:

a means for generating a volume concentration for each anesthetic agent in said anesthetic gas sample; and a means for identifying a primary agent and a secondary agent using minimum alveolar concentration values.

7. A method for identifying the concentration of a plurality of predefined anesthetic agents contained in an anesthetic gas sample comprising the steps of:

placing an anesthetic gas sample in a sample chamber;

irradiating said anesthetic gas sample with light;

detecting an intensity of light emanating from said sample chamber as a result of irradiating said gas sample with said light; and processing said detected intensity to generate a volume concentration for at least two of said predefined anesthetic agents;

identifying one of said at least two predefined components as a primary agent and identifying a second of said at least two predefined components as a secondary agent using minimum alveolar concentration values; and, displaying the identity of said primary agent and said secondary agent on a user display.

8. The method of claim 7 whereon the step of processing further comprises generating a five second running average volume concentration.

9. The method of claim 8 wherein said step of identifying comprises:

determining if the five second volume concentration for any anesthetic gas agent is greater than 0.2 v/v %.

10. The method of claim 8 wherein said step of identifying said primary agent comprises selecting the anesthetic agent with a volume concentration greater than 0.2 v/v % and the highest percentage of its minimum alveolar concentration.

11. The method of claim 10 wherein said step of identifying said secondary agent comprises selecting the anesthetic agent with a volume concentration greater than the greater of 0.3 v/v % or five percent of the five second running average of said primary agent and which has a volume concentration which gives it the second highest percentage of its MAC.

* * * * *